United States Patent
Gonzalez et al.

(10) Patent No.: US 7,276,230 B2
(45) Date of Patent: Oct. 2, 2007

(54) SUNSCREEN COMPOUNDS AND COMPOSITIONS CONTAINING SAME AND METHODS FOR USE THEREOF

(75) Inventors: Anthony D. Gonzalez, Oak Ridge, NJ (US); Andrew H. Pechko, Ridgewood, NJ (US); Glen T. Anderson, Pleasantville, NY (US); Robert E. Kalafsky, Ogdensburg, NJ (US)

(73) Assignee: Avon Products, Inc., New York, NY (US)

( * ) Notice: Subject to any disclaimer, the term of this patent is extended or adjusted under 35 U.S.C. 154(b) by 453 days.

(21) Appl. No.: 10/744,365

(22) Filed: Dec. 23, 2003

(65) Prior Publication Data

US 2005/0136012 A1 Jun. 23, 2005

(51) Int. Cl.
*A61Q 19/04* (2006.01)
*A61Q 19/00* (2006.01)
*A61K 8/02* (2006.01)

(52) U.S. Cl. ............................. 424/59; 60/400; 60/401
(58) Field of Classification Search .................. 424/59, 424/60, 400, 401
See application file for complete search history.

(56) References Cited

U.S. PATENT DOCUMENTS 5,827,509 A * 10/1998 Richard et al. ............... 424/60

* cited by examiner

*Primary Examiner*—Shelley A. Dodson
(74) *Attorney, Agent, or Firm*—Ohlandt, Greeley, Ruggiero & Perle, L.L.P.

(57) ABSTRACT

There is provided a photostable and synergistically enhanced topical sunscreen composition that provides increased substantivity, waterproofness, sweat resistance and rub off resistance. There is further provided methods of enhancing the photostability of a sunscreen active in a topical sunscreen composition, synergistically enhancing the UV absorbance of a topical sunscreen composition having a sunscreen active, and enhancing the substantivity, waterproofness, sweat resistance and rub off resistance in a topical sunscreen composition. The preferred compositions and methods have a sunscreen active, a cosmetically acceptable vehicle, and novel 2-substituted-3,3-diaryl-2-propenoic acid derivatives with [A] a $C_{16}$ to $C_{50}$ straight or branched chain, substituted or un-substituted, conjugated or non-conjugated hydrocarbon, or [B] a siloxane, polysiloxane, organo-modified polysiloxane residue, a group represented by the formula $R^{10}[Si(R^{10})_2]_n$— and $R^{11}$ which is a silicone residue derived from a silicone represented by the formula $R^{11}OH$ having a molecular weight up to about 30,000, wherein each $R^{10}$ is independently selected from the group consisting of alkyl, alkoxy, aryl and aryloxy and n is from 1 to about 500.

57 Claims, 1 Drawing Sheet

Fig. 1

SUNSCREEN COMPOUNDS AND COMPOSITIONS CONTAINING SAME AND METHODS FOR USE THEREOF

BACKGROUND OF THE INVENTION

1. Field of the Invention

The present invention relates to a novel ingredient and the use of same. More particularly, it relates to molecules/compounds that are 2-substituted-3,3-diphenyl-2-propenoic acids reacted with [A] a $C_{16}$ to $C_{50}$ straight or branched chain, substituted or unsubstituted, conjugated or non-conjugated hydrocarbon, or [B] a siloxane, polysiloxane or organo-modified polysiloxane residue. When there is a $C_{16}$ to $C_{50}$ chain and it is also a substituted hydrocarbon, the substitutions to the hydrocarbon chain can be an amine, an amide, a hydroxyl, an alkoxy, an alkyl, a halogen, a nitrogen, a sulfonyl, nitrile, or phenyl. Even more particularly, the present invention relates to the use of the new molecules in sunscreen compositions to provide protection against the harmful effects caused by ultraviolet radiation. The present invention also relates to methods for providing ultraviolet radiation protection while also providing increased UV absorbance, photostabilization, substantivity, waterproofing, water resistance, sweat proofing, sweat resistance, and/or rub off resistance in cosmetic and personal care compositions.

2. Description of the Related Art

Commercial sunscreen compositions commonly employ a sunscreen active, such as a dibenzoylmethane derivative, e.g. butylmethoxydibenzoylmethane (avobenzone). A common problem associated with some sunscreen compositions is a tendency of sunscreen actives, including dibenzoylmethane and/or derivatives thereof, to photodegrade over time from exposure to UV (ultraviolet) light, e.g. lack of photostabilization. This results in an alteration of the UV absorbance of the composition and, thus, a diminution in sunscreen protection for the user during extended exposure to sunlight.

U.S. Pat. No. 5,952,391 relates to sunscreen compositions having dibenzoylmethane sunscreen actives. The compositions have flavone or flavanone derivatives to stabilize the dibenzoylmethane actives.

Current esters of 2-cyano-3,3-diphenyl-2-propenonic acid have short chain alcohols for ease of use. U.S. Pat. No. 6,416,773 modified the commercially available esters by reacting the acid with a cyclic alcohol. This change has resulted in crystalline solids with poor solubility that require the addition of solvents that were not preferred for optimal efficacy, aesthetics, and stability. Consequently, these esters are not ideally suited for cosmetic formulations.

Besides photostabilization, suncare formulations also strive for water, perspiration and wear resistance. Additionally, a desired property of sunscreens is protection from both UVB and UVA wavelengths, as well as increased coverage of the skin.

It is desired to have a sunscreen composition that is photostable and affords the claimed sunscreen protection for an extended period of time. It is also desired to have a sunscreen composition that provides: water, perspiration and wear resistance; photostabilization of dibenzoylmethane and its derivatives and other sunscreens; a synergistic increase in UV absorbance with dibenzoylmethane derivatives; and a cumulative boost of UV absorbance in the erythemal action spectra of UV light. It is further desired to have such a photostable sunscreen composition that affords an enhanced degree of sunscreen protection from a broad spectrum of both UVB and UVA wavelengths, and that also offers improved coverage of the skin.

SUMMARY OF THE INVENTION

It is an object of the present invention to provide a molecule/compound that imparts water resistance to a personal care composition, preferably a suncare or insect repellent and/or a combination sunscreen/insect repellent product.

It is another object of the present invention to provide such a molecule/compound that imparts photostability to a sunscreen composition.

It is still another object of the present invention to provide such a molecule/compound in which dibenzoylmethane derivatives are photostabilized by the unique molecule.

It is yet another object of the present invention to provide such a molecule/compound that has a synergistic effect with sunscreens to provide enhanced UV absorbance upon increased exposure to ultraviolet light.

It is a further object of the present invention to provide a method of incorporating this molecule/compound into a personal care composition, preferably a suncare product or an outdoor protection product.

It is still a further object of the present invention to provide such a method in which this molecule/compound is incorporated into a suncare product that is water resistant or waterproof, sweat resistant or sweatproof, and/or photostable.

These and other objects and advantages of the present invention are achieved by a composition with improved photostability and enhanced SPF. More preferably, the composition also has water resistant properties. The composition may be cream, gel, liquid, lotion, serum, towlette impregnated with the composition, mousse, patch, sachet, powder, balm, stick or spray form. The compounds of the present invention have the following general formula (I):

wherein $X_1$, $X_2$ and $X_3$ are independently chosen from a group of the following constituents: cyclic and acyclic, saturated and unsaturated, substituted and unsubstituted, alkyl, aryl, amide, amine, hydroxyl, alkoxyl, halogen, hydrogen, carboxyl, nitrile, nitro, sulfonyl, anionic or cationic groups. Preferred substituents include methyl, ethyl, propyl, cyclopropyl, butyl, cyclobutyl, hexyl, cyclohexyl, heptyl, cycloheptyl, octyl, cyclooctyl, chlorine, bromine, sulfate, phosphate, methoxy, ethoxy, propoxy, butoxy, cyano, cyanato, cyanamino groups, with cyano and cyanato being most preferred;

$X_4$ is chosen from NH, NR, O and S, with O being most preferred;

Y is chosen from NH, NR, O and S, with O being most preferred. $X_4$=O and Y=O are most preferred. R is a $C_1$ to $C_{30}$ alkyl, preferably $C_1$ to $C_{18}$, substituted or unsubstituted, preferably linear; and Z may be either [A] a $C_{16}$ to $C_{50}$ straight or branched chain, substituted or unsubstituted, conjugated or non-conjugated hydrocarbon or [B] a siloxane, polysiloxane or organo-modified polysiloxane residue. When there is a $C_{16}$ to $C_{50}$ chain and it is also a substituted hydrocarbon, the substitutions to the hydrocarbon chain can be an amine, an amide, a hydroxyl, an alkoxy, an alkyl, a halogen, a nitrogen, a sulfonyl, nitrile, or phenyl. Preferred compounds have esters of 2-cyano-3,3-diphenyl-2-propenoic acid with a $C_{16}$ to $C_{50}$ straight or branched chain, substituted or un-substituted, conjugated or non-conjugated hydrocarbon. When there is a $C_{16}$ to $C_{50}$ chain, it is preferred that Z be a $C_{16}$ to $C_{40}$ alkyl, $C_{17}$ to $C_{50}$ alkyl, $C_{17}$ to $C_{40}$ alkyl, $C_{18}$ to $C_{50}$ alkyl, $C_{18}$ to $C_{40}$ alkyl, $C_{18}$ to $C_{50}$ alkyl, $C_{19}$ to $C_{40}$ alkyl, $C_{20}$ to $C_{50}$ alkyl, $C_{20}$ to $C_{40}$ alkyl, $C_{21}$ to $C_{50}$ alkyl, $C_{21}$ to $C_{40}$ alkyl, $C_{22}$ to $C_{50}$ alkyl or $C_{22}$ to $C_{40}$ alkyl. Also, any combinations of any alkyls within the $C_{16}$ to $C_{50}$ alkyl range are also contemplated by the present invention. Particularly preferred are $C_{20}$ to $C_{40}$ alkyls.

BRIEF DESCRIPTION OF THE DRAWINGS

These and other embodiments of the present invention will be appreciated by referring to the drawings that include

DETAILED DESCRIPTION OF THE INVENTION

The present invention provides a unique class of molecules or compounds that can be incorporated into a cosmetic or personal care composition or product intended for protecting the skin against UV radiation. The composition can be a suncare product and/or an insect repellent product. More preferably, the composition is a sunscreen product.

The compounds of the present invention have the following general formula (I):

wherein $X_1$, $X_2$ and $X_3$ are independently chosen from a group of the following constituents: cyclic and acyclic, saturated and unsaturated, substituted and unsubstituted, alkyl, aryl, amide, amine, hydroxyl, alkoxyl, halogen, hydrogen, carboxyl, nitrile, nitro, sulfonyl, anionic or cationic groups. Preferred substituents include methyl, ethyl, propyl, cyclopropyl, butyl, cyclobutyl, hexyl, cyclohexyl, heptyl, cycloheptyl, octyl, cyclooctyl, chlorine, bromine, sulfate, phosphate, methoxy, ethoxy, propoxy, butoxy, cyano, cyanato, cyanamino groups, with cyano and cyanato being most preferred;

$X_4$ is chosen from NH, NR, O and S, with O being most preferred;

Y is chosen from NH, NR, O and S, with O being most preferred. $X_4$=O and Y=O are most preferred. R is a $C_1$ to $C_{30}$ alkyl, preferably $C_1$ to $C_{18}$, substituted or unsubstituted, preferably linear; and Z may be either [A] a $C_{16}$ to $C_{50}$ straight or branched chain, substituted or unsubstituted, conjugated or non-conjugated hydrocarbon or [B] a siloxane, polysiloxane, organo-modified polysiloxane residue, a group represented by the formula: $R^{10}[Si(R^{10})_2]_n$— and $R^{11}$ which is a silicone residue derived from a silicone represented by the formula $R^{11}OH$ having a Molecular Weight up to about 30,000, wherein each $R^{10}$ is independently selected from the group consisting of alkyl, alkoxy, aryl and aryloxy and n is from 1 to about 500. $R^{11}OH$ can be a substituted or unsubstituted siloxane or a substituted or unsubstituted organosiloxane.

The preferred compounds of the present invention are 2-substituted-3,3-diphenyl-2-propenoic acid derivatives of general formula (I):

wherein $X_1$, $X_2$ and $X_3$ are independently chosen from a group of the following constituents: cyclic and acyclic, saturated and unsaturated, substituted and unsubstituted, alkyl, aryl, amide, amine, hydroxyl, alkoxyl, halogen, hydrogen, carboxyl, nitrile, nitro, sulfonyl, anionic or cationic groups. Preferred substituents include methyl, ethyl, propyl, cyclopropyl, butyl, cyclobutyl, hexyl, cyclohexyl, heptyl, cycloheptyl, octyl, cyclooctyl, chlorine, bromine, sulfate, phosphate, methoxy, ethoxy, propoxy, butoxy, cyano, cyanato, cyanamino groups, with cyano and cyanato being most preferred;

$X_4$ is O;

Y is O.

Z may be either [A] a $C_{16}$ to $C_{50}$ straight or branched chain, substituted or unsubstituted, conjugated or non-conjugated hydrocarbon or [B] a siloxane, polysiloxane, organo-modified polysiloxane residue, a group represented by the formula: $R^{10}[Si(R^{10})_2]_n$— and $R^{11}$ which is a silicone residue derived from a silicone represented by the formula $R^{11}OH$ having a Molecular Weight up to about 30,000, wherein each $R^{10}$ is independently selected from the group consisting of alkyl, alkoxy, aryl and aryloxy and n is from 1 to about 500. $R^{11}OH$ can be a substituted or unsubstituted siloxane or a substituted or unsubstituted organosiloxane.

For the compounds, as well as the preferred compounds, the silicone residues represented by the formula $R^{11}$ is $R^{10}[Si(R^{10})_2]_n$—, are derived from the corresponding silicone alcohols, i.e., hydroxy group containing silicones, including silicone alcohols, such as, hydroxy substituted and hydroxy terminated silicones.

Examples of hydroxyl functional silicones include Dimethiconol, which is sold under the trade name of Dow Corning 2-9023, Silicone Fluid NM 201-50.000, Unisil SF-R, silanol, methylsilanol, other organomodified silanols, such as, Dow Corning 1248 fluid, and a polydimethylsiloxane polymer having a terminal silanol functionality, such as, for example, 2-1273 fluid from Dow Corning.

When there is a $C_{16}$ to $C_{50}$ chain and it is also a substituted hydrocarbon, the substitutions to the hydrocarbon chain can be an amine, an amide, a hydroxyl, an alkoxy, an alkyl, a halogen, a nitrogen, a sulfonyl, nitrile, or phenyl. Preferred compounds have esters of 2-cyano-3,3-diphenyl-2-propenoic acid with a $C_{16}$ to $C_{50}$ straight or branched chain, substituted or un-substituted, conjugated or non-conjugated hydrocarbon. When there is a $C_{16}$ to $C_{50}$ chain, it is preferred that Z be a $C_{16}$ to $C_{40}$ alkyl, $C_{17}$ to $C_{50}$ alkyl, $C_{17}$ to $C_{40}$ alkyl, $C_{18}$ to $C_{50}$ alkyl, $C_{18}$ to $C_{40}$ alkyl, $C_{19}$ to $C_{50}$ alkyl, $C_{19}$ to $C_{40}$ alkyl, $C_{20}$ to $C_{50}$ alkyl, $C_{20}$ to $C_{40}$ alkyl, $C_{21}$ to $C_{50}$ alkyl, $C_{21}$ to $C_{40}$ alkyl, $C_{22}$ to $C_{50}$ alkyl or $C_{22}$ to $C_{40}$ alkyl. Also, any combinations of any alkyls within the $C_{16}$ to $C_{50}$ alkyl range are also contemplated by the present invention. Particularly preferred are $C_{20}$ to $C_{40}$ alkyls.

The novel molecules or compounds are 2-substituted-3,3-diphenyl-2-propenoic acids reacted with [A] a $C_{16}$ to $C_{50}$ straight or branched chain, substituted or unsubstituted, conjugated or non-conjugated hydrocarbon, or [B] a siloxane, polysiloxane or organo-modified polysiloxane residue. When there is a $C_{16}$ to $C_{50}$ chain and it is also a substituted hydrocarbon, the substitutions to the hydrocarbon chain can be an amine, an amide, a hydroxyl, an alkoxy, an alkyl, a halogen, a nitrogen, a sulfonyl, nitrile, or phenyl. The esters can be used in a variety of personal care products.

Previously described short chain or cyclic esters of 2-cyano-3,3-diphenyl-2-propenoic acid absorb predominantly in the UVB spectrum, while long chain esters exhibited absorbance in the UVA and UVB regions as well as improved compatibility with standard cosmetic oils.

It has been unexpectedly discovered according to the present invention that a composition having 2-substituted-3,3-diphenyl-2-propenoic acids reacted with [A] a $C_{16}$ to $C_{50}$ straight or branched chain, substituted or unsubstituted, conjugated or non-conjugated hydrocarbon, or [B] a siloxane, polysiloxane or organo-modified polysiloxane residue, which have a large molecular configuration, provides superior substantivity, waterproofing and wear resistance as compared to short chain or cyclic esters of 2-cyano-3,3-diphenyl-2-propenoic acid that are currently known in the art. It was surprisingly found that the preferred embodiment has an ideal UV absorbance for use in personal UV protection products and provides broad spectrum protection. It was also surprisingly found that the present invention provides for a synergistic increase in UV absorbance upon long term UV exposure when used in combination with dibenzoylmethane derivatives and/or other sunscreen actives. Additionally, superior photostabilization of the dibenzoylmethane derivative was noted. Previously described short chain or cyclic esters of 2-cyano-3,3-diphenyl-2-propenoic acid absorb predominantly in the UVB spectrum. Furthermore, the above described changes to the Z component of the molecule provide a functional molecule that is easy to work with in cosmetic formulations.

The present compositions having 2-substituted-3,3-diphenyl-2-propenoic acids reacted with [A] a $C_{16}$ to $C_{50}$ straight or branched chain, substituted or unsubstituted, conjugated or non-conjugated hydrocarbon, or [B] a siloxane, polysiloxane or organo-modified polysiloxane residue, provide for increased substantivity, water and rub off resistance in personal care preparations. The present composition provides for a synergistic increase in UV absorbance upon long term UV exposure when used in combination with dibenzoylmethane derivatives and/or other sunscreen actives including Mexoryl SX (terephthalylidene dicamphor sulfonic acid and salts thereof), PABA (para aminobenzoic acid) and its derivatives, cinoxate, dioxybenzone, homosalate, menthylanthranilate, octocrylene, octyl methoxycinnamate, octyl salicylate, oxybenzone, padimate O, phenylbenzimidazole sulfonic acid, sulisobenzone, titanium dioxide, zinc oxide, trolamine salicylate, and octyl triazone. Additionally, the composition provides for photostabilization of the dibenzoylmethane derivative. The preferred entity $C_{20}$-$C_{40}$ cyano diphenyl propionate provides for substantial UV absorbance in the erythemal action spectrum. In addition, the preferred entity preferably offers a balanced UVA/UVB ratio of about 0.1 to about 0.9, more preferably about 0.25 to about 0.75, and most preferably about 0.4 to about 0.6.

The present composition may have one or more additional sunscreen actives. Such other sunscreen actives may be organic or inorganic, and/or water-soluble or oil soluble. Such actives include those with UVA and/or UVB absorbance from 290 to 400 nanometer solar radiation. Such sunscreen actives include, but are not limited to, one or more of the following: DEA methoxycinnamate, drometrizole trisiloxane, oxybenzone, octyl methoxycinnamate, octyl salicylate, homomenthyl salicylate, octyl dimethyl PABA, TEA salicylate, 4-methyl benzilidene camphor, terephthalydiene dicamphor sulfonic acid, ethyl PABA, hydroxy methylphenyl benzotriazole, methylene bis-benzotriazoyltetramethylbutylphenol, bis-ethylhexyloxyphenol methoxyphenol triazine, zinc oxide, titanium dioxide or any derivatives, or any combinations thereof. Other useful sunscreen actives include those disclosed in U.S. Pat. Nos. 5,000,937 and 6,440,402, which sunscreen actives are incorporated herein by reference.

The compounds according to the present invention can be prepared by the reaction of a compound of formula (I), wherein the group —Y—Z together represents a single halide, such as a chloride, with the hydroxy functional hydrocarbon or siloxane compound, in the presence of an aqueous base when $X_4$ is oxygen, and, when $X_4$ is NH, NR or S, under anhydrous conditions, that are generally used for such reactions. Thus, Schotten-Bauman reaction conditions can be used when $X_4$ is O, and modified Schotten-Bauman reaction conditions can be used when $X_4$ is NH, NR, or S, provided anhydrous reaction conditions are maintained.

Preferred bases are those that are capable of removing the hydrogen halide formed during the reaction. Such bases include hindered amines, such as, 2,2,6,6-tetramethylpiperidenes, diazabicyclooctanes, such as, DABCO, diazabicyclononanes, diazabicyclodecanes, trioctylamine, tridecylamine, tridodecylamine, pentamethyl guanidine, lutidine, proton sponges, such as, 1,10-bis(dimethylamino)naphthalene, basic alumina, basic silica gel, and the like. Aqueous alkali can be used for the Schotten-Bauman reaction.

The present invention provides the suncare formulator with a multifunctional molecule or compound for the formulation of all types of suncare products. As discussed above, the present composition can provide water, sweat and wear resistance, photostabilization of dibenzoylmethane and its derivatives and other sunscreens, a synergistic increase in UV absorbance to provide an ideal absorbency when used in combination with dibenzoylmethane derivatives. It also provides a cumulative boost of UV absorbance in the erythemal action spectra of UV light. The present composition also provides protection from both UVB and UVA wavelengths. The large size of this molecule can help lead to more even coverage of the skin and more active chromophore left on the surface of the skin.

The large molecular configuration of the compound or molecule of the present invention provides for superior substantivity, waterproofing, sweatproofing and wear resistance as compared to the aforementioned short chain or cyclic esters of 2-cyano-3,3-diphenyl-2-propenoic acid which are currently known in the art.

Figure 1:
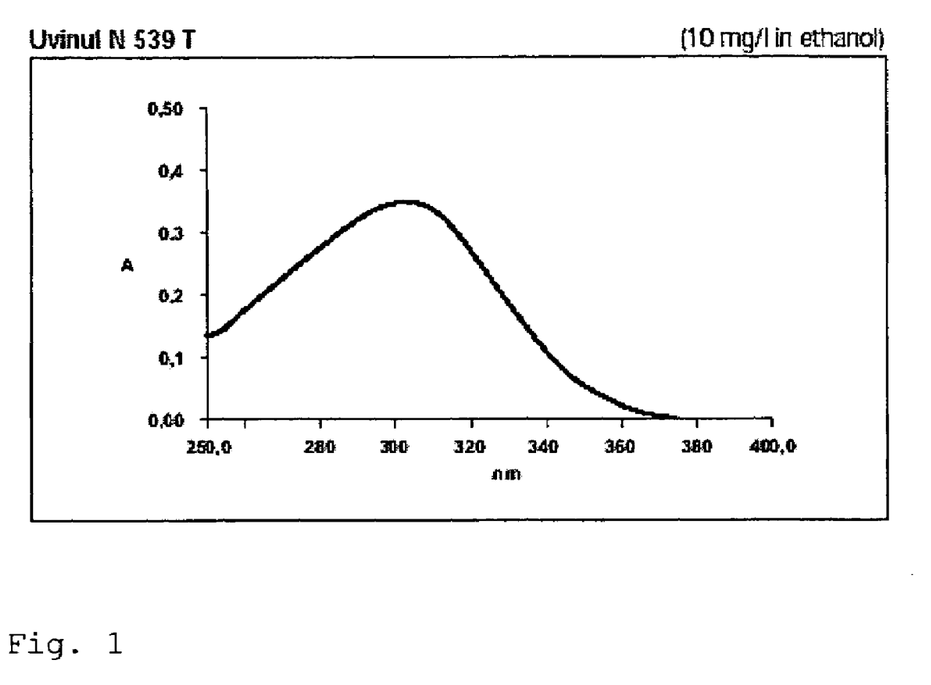
FIG. 1 is a graph illustrating the UV absorbance of UVINUL N 539.

A typical sunscreen active known in the art is octocrylene and has the trade name UVINUL N 539 T. Octocrylene's chemical structure is:

UVINUL N 539 T is an oil-miscible UV-B filter used in suncare preparations. As it is miscible with many cosmetic oils, it can be easily incorporated in the oily phase of an emulsion. Because it is hydrophobic and oil-soluble, it is commonly used for water-resistant and water-repellant formulations. UVINUL N 539 T is commonly combined with other oil-soluble UV filters to obtain high SPF values. FIG. 1 is a graph illustrating the UV absorbance of UVINUL N 539 T, where the y axis is absorbance and the x axis is wavelength in nanometers.

Table 1 shows the effects of UV exposure on compositions of the present invention in combination with the dibenzoylmethane derivative, avobenzone. Samples were exposed to UV radiation produced by a 125W Xenon Arc Lamp at 75W power. The UV absorbing properties of the composition were measured every five (5) minutes for a total exposure of one (1) hour.

TABLE 1

(Scans taken every 300 seconds)

| Scan | Elapsed Time (sec.) | Δ SPF | Δ UVA/ UVB Ratio | Δ UVA PF | Δ UVA PF- | ΔCrit. Lamda | Δ Cummul. Absorbance |
|---|---|---|---|---|---|---|---|
| 1 | 0 | 47.6 | 1.12 | 65.1 | 56.5 | 389.2 | 194 |
| 2 | 300 | 70.4 | 1.07 | 84.4 | 78.4 | 389.1 | 208 |
| 3 | 600 | 74.0 | 1.05 | 84.4 | 80.9 | 389.1 | 209 |
| 4 | 900 | 75.0 | 1.05 | 83.8 | 81.1 | 389.1 | 209 |
| 5 | 1200 | 74.8 | 1.05 | 83.2 | 80.5 | 389.1 | 209 |
| 6 | 1500 | 73.9 | 1.05 | 82.5 | 79.9 | 389.1 | 208 |
| 7 | 1800 | 74.6 | 1.05 | 82.4 | 80.2 | 389.1 | 208 |
| 8 | 2100 | 74.3 | 1.05 | 82.2 | 79.9 | 389.1 | 208 |
| 9 | 2400 | 74.0 | 1.05 | 82.2 | 79.7 | 389.1 | 208 |
| 10 | 2700 | 73.6 | 1.05 | 81.5 | 79.1 | 389.1 | 208 |
| 11 | 3000 | 73.9 | 1.05 | 81.4 | 79.2 | 389.1 | 208 |
| 12 | 3300 | 73.8 | 1.04 | 81.5 | 79.7 | 389.1 | 208 |

As shown in Table 1, over the course of twelve scans taken at 300 second intervals, a 55% improvement in overall SPF activity is demonstrated with the present invention. There is also a 25% improvement in UV-A activity, as well as a 41% improvement in erythemal protection. The change in critical lambda or critical wavelength is −0.025%. The change in cumulative absorbance is +6.7%.

Table 2 below sets forth test data from the negative control (i.e., previously modified (cyclic) octocrylene alone).

TABLE 2

Photostability in Solution

| Parameter | Control | Cyclic Modified Octocrylene |
|---|---|---|
| Change in SPF | −80.41% | 121.60% |
| Change in UVA/UVB | −51.64% | −34.00% |
| Change in UVAPF | −91.98% | 1167.65% |
| Change in Erythemal UVAPF | −87.86% | 242.42% |
| Change in Critical Wavelength | −1.84% | −1.61% |
| Change in Absorbance | −80.65% | 103.74% |

The cyclic modified octocrylene is identified in the aforementioned U.S. Pat. No. 6,416,773.

The present invention is also directed to compositions containing the novel compounds, especially cosmetic and personal care composition, and most especially sunscreen compositions. The present compositions may include any cosmetic vehicle known in the art. Suitable vehicles include, but are not limited to, surfactant/cleansing systems, oral care products, OTC drugs, artificial tanning, beach/suncare, footcare, patches, wipes, aqueous products, anhydrous products, emulsions, spray products, antiperspirant/deodorant (ap/deo) products, fragranced products, analgesics, insect repellents, jelly fish repellents, poison ivy, oak and sumac protectants, cosmetic sticks, hair care products, conditioners, shampoos, hair colors, styling aids, decorative cosmetics including make-ups, nail polish, pressed powders, mascara, eyeliners, tattoos/body art, lipsticks, lip balms, and concentrates thereof.

The composition can be made into any suitable product form. Such product forms include, but are not limited to, an aerosol, balm, cream, gel, lotion, serum, mousse, patch, pomade, pump spray, roll-on, solution, stick or towelette.

Suitable components of the cosmetic composition may include but are not limited to one or more of the following: vegetable oils; esters such as octyl palmitate, C12-15 alkyl benzoate, isopropyl myristate and isopropyl palmitate; ethers such as dicapryl ether and dimethyl isosorbide; alcohols such as ethanol and isopropanol; fatty alcohols such as cetyl alcohol, stearyl alcohol and behenyl alcohol; isoparaffins such as isooctane, isododecane and isohexadecane; silicone oils such as dimethicones, cyclic silicones, and polysiloxanes; hydrocarbon oils such as mineral oil, petrolatum, isoeicosane and polyisobutene; polyols such as propylene glycol, ethoxydiglycol, glycerin, butylene glycol, pentylene glycol and hexylene glycol; an elastomer, or any combinations thereof.

The amount of the novel compound of the present invention to be used in a particular formulation depends on the level of dibenzoylmethane derivative to be stabilized. The compounds of the present invention may be incorporated into a sunscreen composition at a ratio from 0.05:5.0 to 5.0:0.05 on a weight to weight basis of sunscreen to novel compound. A more preferred ratio is from 0.4:4.0 to 4.0:0.4 and most preferred is 1:3.0 to 3.0:1.0.

Optionally, the present composition may include one or more of the following ingredients: anesthetics, anti-allergenics, antifungals, antimicrobials, anti-inflammatories, antiseptics, chelating agents, botanical extracts, colorants, depigmenting agents, emollients, exfolients, film formers, fragrances, humectants, insect repellents (especially ethyl butylacetylaminopropionate (IR3535) and 1-piperidinecarboxylic acid 2-(2-hydroxyethyl)-1-methylpropylester and its isomers (Bayer Chemical—Bayrepel KBR 3023), jelly fish repellents, poison ivy, oak and sumac protectants, lubricants, moisturizers, pharmaceutical agents, preservatives, skin protectants, skin penetration enhancers, stabilizers, surfactants, thickeners, viscosity modifiers, vitamins, or any combinations thereof. Film formers are particularly preferred.

The present compositions may also have one or more insect repellent actives. Such actives include, but are not limited to, N,N diethyl-m-toluamide (DEET), ethyl butylacetylaminopropionate (IR3535 by Merck Co.), 1-piperidinecarboxylic acid 2-(2-hydroxyethyl)-1-methylpropylester and its isomers (Bayer Chemical—Bayrepel KBR 3023), 1-{3-cyclohexen-1-ylcarbonyl}-2-methylpiperidine and its isomers (racemate AI3-37220), oil of citronella, soy bean oil, lemon grass oil, geranium/geraniol oil, neem oil, nepetalactone and its isomers and other natural essential oils, p-menthane-3,8-diol, oil of rue (IBI-246 or any mixtures thereof. Other useful actives are disclosed in U.S. Pat. Nos. 5,130,136 and 5,698,209, which actives from those patents are incorporated herein by reference. Preferred insect repellent actives are DEET, IR3535, KBR 3023, nepetalactone and oil of citronella.

Suitable additional film formers may include poly(vinyl pyrrolidone/1-triacontene) (Tricontanyl PVP), acrylate copolymer, acrylic $C_{12-22}$ alkyl methacrylate copolymer, acrylate/octylacrylamide copolymer, acrylate/VA copolymer, amodimethicone, AMP/acrylate copolymer, behenyl beeswax, behenyl/isostearyl, beeswax, butylated PVP, butyl ester of PVM/MA copolymer, calcium/sodium PVM/MA copolymer, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, hexanediol beeswax, $C_{30-38}$ olefin/isopropyl maleate/MA copolymer, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, and vinyldimethicone, or any combinations thereof.

The present compositions may also have one or more suitable additives. Such additives include, but are not limited to, barium sulfate, silica, nylon polymethylmethacrylate, fiber, plastic, polyethylene, polypropylene, PET, PVC, polyester, protein, colorant/pigment including photo-chromic and thermo-chromic colorant/pigment, or any combinations thereof.

The following is an example of a basic composition according to the present invention.

EXAMPLE 1

| Ingredient | About wt % |
| --- | --- |
| avobenzone | 0.25-3% |
| $C_{20}$-$C_{40}$ cyano diphenyl propionate | 0.5-6% |
| octinoxate | 0.5-7.5% |
| octisalate | 0.25-5% |
| emulsifier | 0.1-7% |
| co-emulsifier | 0.1-5% |
| emollient | 0.0-10% |
| insect repellent | 5-35% |
| waterproofing polymer | 0.0-5% |
| preservative | QS |
| water | QS to 100% |

The following is an example of a particular composition according to the present invention.

EXAMPLE 2

| Ingredient | About wt % |
| --- | --- |
| avobenzone | 0.25-3% |
| $C_{20}$-$C_{40}$ cyano diphenyl propionate | 0.5-6% |
| oxybenzone | 0.5-6% |
| homosalate | 0.25-5% |
| emollient | 0.0-10% |
| ethanol | QS to 100% |
| waterproofing polymer | 0.0-5% |

The present invention having been described with particular reference to the preferred forms thereof, it will be obvious that various changes and modifications may be made herein without departing from the spirit and scope of the present invention as defined in the appended claims.

What is claimed is:

1. A topical sunscreen composition comprising:
   at least one sunscreen active;
   a cosmetically acceptable vehicle; and
   a compound of the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is selected from the group consisting of NH, NR, O and S, Y is selected from the group consisting of NH, NR, O and S, R is a $C_1$ to $C_{30}$ alkyl, substituted or unsubstituted, and Z is a $C_{16}$ to $C_{50}$ straight or branched chain, substituted or unsubstituted, conjugated or non-conjugated hydrocarbon.

2. The composition of claim 1, wherein said $X_1$, $X_2$ and $X_3$ are independently selected from the group consisting of methyl, ethyl, propyl, cyclopropyl, butyl, cyclobutyl, hexyl, cyclohexyl, heptyl, cycloheptyl, octyl, cyclooctyl, chlorine, bromine, sulfate, phosphate, methoxy, ethoxy, propoxy, butoxy, cyano, cyanato, and cyanamino groups.

3. The composition of claim 1, wherein said $X_4$ is O.

4. The composition of claim 1, wherein said Y is O.

5. The composition of claim 1, wherein said Z is a $C_{16}$ to $C_{50}$ chain.

6. A topical sunscreen composition comprising:
at least one sunscreen active;
a cosmetically acceptable vehicle; and
a 2-substituted-3,3-diphenyl-2-propenoic acid derivative of the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups,
$X_4$ is O,
Y is O, and
Z is a $C_{16}$ to $C_{50}$ straight or branched chain, substituted or unsubstituted, conjugated or non-conjugated hydrocarbon.

7. The composition of claim 6, wherein the $R_{11}OH$ is selected from the group consisting of a substituted or unsubstituted siloxane and a substituted or unsubstituted organosiloxane.

8. The composition of claim 6, wherein said $X_1$, $X_2$ and $X_3$ are independently selected from the group consisting of methyl, ethyl, propyl, cyclopropyl, butyl, cyclobutyl, hexyl, cyclohexyl, heptyl, cycloheptyl, octyl, cyclooctyl, chlorine, bromine, sulfate, phosphate, methoxy, ethoxy, propoxy, butoxy, cyano, cyanato, and cyanamino groups.

9. The composition of claim 6, wherein said Z is a $C_{16}$ to $C_{50}$ chain.

10. The composition of claim 9, wherein said $C_{16}$ to $C_{50}$ chain is a substituted hydrocarbon.

11. The composition of claim 6, wherein said Z is a $C_{18}$ to $C_{50}$ alkyl.

12. The composition of claim 6, wherein said Z is a $C_{18}$ to $C_{40}$ alkyl.

13. The composition of claim 6, wherein said Z is a $C_{20}$ to $C_{50}$ alkyl.

14. The composition of claim 6, wherein said Z is a $C_{20}$ to $C_{40}$ alkyl.

15. The composition of claim 6, wherein said Z is a $C_{22}$ to $C_{50}$ alkyl.

16. The composition of claim 6, wherein said Z is a $C_{22}$ to $C_{40}$ alkyl.

17. The composition of claim 6, wherein said substituted hydrocarbon has a substitution to the hydrocarbon chain selected from the group consisting of amine, amide, hydroxyl, alkoxy, alkyl, halogen, nitrogen, sulfonyl, nitrile, and phenyl.

18. The composition of claim 6, wherein said 2-substituted-3,3-diphenyl-2-propenoic acid derivative of said general formula (I) is the ester of 2-cyano-3,3-diphenyl-2-propenoic acid with a $C_{16}$ to $C_{50}$ straight or branched chain, substituted or un-substituted, conjugated or non-conjugated hydrocarbon.

19. The composition of claim 18, wherein said ester of 2-cyano-3,3-diphenyl-2-propenoic acid with $C_{16}$ to $C_{50}$ straight or branched chain, substituted or un-substituted, conjugated or non-conjugated hydrocarbon is $C_{20}$-$C_{40}$ cyano diphenyl propionate.

20. The composition of claim 6, wherein the at least one sunscreen active is selected from the group consisting of dibenzoylmethane, terephthalylidene dicamphor sunfonic acid, PABA, cinoxate, dioxybenzone, homosalate, menthylanthranilate, octocrylene, octyl methoxycinnamate, octyl salicylate, oxybenzone, padimate O, phenylbenzimidazole sulfonic acid, sulisobenzone, titanium dioxide, zinc oxide, trolamine salicylate, octyl triazone, DEA methoxycinnamate, drometrizole trisiloxane, oxybenzone, octyl methoxycinnamate, octyl salicylate, homomenthyl salicylate, octyl dimethyl PABA, TEA salicylate, 4-methyl benzilidene camphor, ethyl PABA, hydroxy methylphenyl benzotriazole, methylene bis-benzotriazoyltetramethyblbutylphenol, zinc oxide, titanium dioxide, bis-ethylhexyloxyphenol methoxyphenol triazine, and any derivatives thereof, and any combinations thereof.

21. The composition of claim 6, wherein the at least one sunscreen active is dibenzoylmethane or a derivative thereof.

22. The composition of claim 21, wherein said 2-substituted-3,3-diphenyl-2-propenoic acid derivative is present at a ratio from about 0.05:5.0 to about 5.0:0.05 on a weight to weight basis of sunscreen to 2-substituted-3,3-diphenyl-2-propenoic acid derivative.

23. The composition of claim 6, wherein said vehicle is selected from the group consisting of surfactant/cleansing system, oral care product, OTC drug, artificial tanning product, beach/suncare product, footcare product, patch, wipe, aqueous product, anhydrous product, emulsion, spray product, antiperspirant/deodorant product, fragranced product, analgesic, insect repellent, jelly fish repellent, poison ivy, oak and sumac protectant, cosmetic stick, balm, hair care product, conditioner, shampoo, hair color, styling aid, decorative cosmetic, make-up, nail polish, pressed powder, mascara, eyeliner, tattoo/body art, lipstick and concentrates thereof, and any combinations thereof.

24. The composition of claim 6, further comprising a component selected from the group consisting of vegetable oil, second ester, ether, alcohol, fatty alcohol, isoparaffin, silicone oil, hydrocarbon oil, polyol, elastomer, water, and any combinations thereof.

25. The composition of claim 6, wherein said 2-substituted-3,3-diphenyl-2-propenoic acid derivative is present in an amount sufficient to synergistically enhance UV absorbance of the composition.

26. The composition of claim 6, wherein said 2-substituted-3,3-diphenyl-2-propenoic acid derivative is present in an amount sufficient to enhance the photostability of said at least one sunscreen active.

27. The composition of claim 6, wherein said 2-substituted-3,3-diphenyl-2-propenoic acid derivative is present in an amount sufficient to enhance the water, perspiration and wear resistance of the composition.

28. The composition of claim 6, wherein said 2-substituted-3,3-diphenyl-2-propenoic acid derivative is present in an amount sufficient to increase UV absorbance in the erythemal action spectra of UV light of the composition.

29. The composition of claim 6, wherein said 2-substituted-3,3-diphenyl-2-propenoic acid derivative is present in an amount to provide even coverage of skin.

30. The composition of claim 6, further comprising a film former.

31. The composition of claim 30, wherein said film former is selected from the group consisting of poly(vinyl pyrrolidone/1-triacontene), acrylate copolymer, acrylic $C_{12-22}$ alkyl methacrylate copolymer, acrylate/octylacrylamide copolymer, acrylate/VA copolymer, amodimethicone, AMP/acrylate copolymer, behenyl beeswax, behenyl/isostearyl, beeswax, butylated PVP, butyl ester of PVM/MA copolymers, calcium/sodium PVM/MA copolymer, dimethicone, dimethicone copolyol, dimethicone/mercaptopropyl methicone copolymer, dimethicone propylethylenediamine behenate, dimethicolnol ethylcellulose, ethylene/acrylic acid copolymer, ethylene/MA copolymer, ethylene/VA copolymer, fluoro $C_{2-8}$ alkyldimethicone, hexanediol beeswax, $C_{30-38}$ olefin/isopropyl maleate/MA copolymer, hydrogenated styrene/butadiene copolymer, hydroxyethyl ethylcellulose, isobutylene/MA copolymer, laurylmethicone copolyol, methyl methacrylate crosspolymer, methylacryloyl ethyl betaine/acrylates copolymer, microcrystalline wax, nitrocellulose, octadecene/MA copolymer, octadecene/maleic anhydride copolymer, octylacrylamide/acrylate/butylaminoethyl methacrylate copolymer, oxidized polyethylene, perfluoropolymethylisopropyl ether, polyacrylic acid, polyethylene, polymethyl methacrylate, polypropylene, polyquaternium-10, polyquaternium-11, polyquaternium-28, polyquaternium-4, PVM/MA decadiene crosspolymer, PVM/MA copolymer, PVP, PVP/decene copolymer, PVP/eicosene copolymer, PVP/hexadecene copolymer, PVP/MA copolymer, PVP/VA copolymer, silica dimethyl silylate, sodium acrylate/vinyl alcohol copolymer, stearoxy dimethicone, stearoxytrimethylsilane, stearyl alcohol, stearylvinyl ether/MA copolymer, styrene/DVB copolymer, styrene/MA copolymer, tetramethyl tetraphenyl trisiloxane, tricontanyl trimethyl pentaphenyl trisiloxane, trimethylsiloxysilicate, VA/crotonates copolymer, VA/crotonates/vinyl proprionate copolymer, VA/butyl maleate/isobornyl acrylate copolymer, vinyl caprolactam/PVP/dimethylaminoethyl methacrylate copolymer, vinyldimethicone, diethylhexyl sebacate, and any combinations thereof.

32. The composition of claim 6, further comprising an insect repellent selected from the group consisting of N,N-diethyl-m-toluamide, ethyl butylacetylaminopropionate, hydroxyethyl 1-piperidinecarboxylic acid 2-(2-hydroxyethyl)-1-methylpropylester and its isomers, oil of citronella, nepetalactone and its isomers, soy bean oil, lemon grass oil, geraniol/geraniol oil, neem oil, p-menthane-3,8-diol, oil of rue, 1-{3-cyclohexen-1-ylcarbonyl}-2-methylpiperidine and its isomers, and any combinations thereof.

33. The composition of claim 6, wherein the composition is in the form selected from the group consisting of an aerosol, balm, cream, gel, lotion, serum, mousse, patch, pomade, pump spray, roll-on, solution, stick, towelette, surfactant/cleansing system, oral care product, OTC drug, artificial tanning product, beach/suncare product, footcare product, patch, wipe, aqueous product, anhydrous product, emulsion, spray product, antiperspirant/deodorant product, fragranced product, analgesic, insect repellent, jelly fish repellents, poison ivy, oak and sumac protectants, cosmetic stick, balm, hair care product, conditioner, shampoo, hair color, styling aid, decorative cosmetic, make-up, nail polish, pressed powder, mascara, eyeliner, tattoo/body art, lipstick and concentrates thereof, and any combinations thereof.

34. The composition of claim 6, wherein Z is $C_{16}$ to $C_{50}$ straight or branched chain, substituted or unsubstituted, conjugated or non-conjugated hydrocarbon.

35. A method of enhancing the substantivity, waterproofness, sweat resistance and rub off resistance in a topical sunscreen composition having a sunscreen active and a cosmetically acceptable vehicle, the method comprising introducing into the composition an amount of a compound having the following general formula (I):

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is selected from the group consisting of NH, NR, O and S, Y is selected from the group consisting of NH, NR, O and S, and Z is a $C_{16}$ to $C_{50}$ straight or branched chain, substituted or unsubstituted, conjugated or non-conjugated hydrocarbon.

36. A method of enhancing the substantivity, waterproofness, sweat resistance and rub off resistance in a topical sunscreen composition having a sunscreen active and a cosmetically acceptable vehicle, the method comprising introducing into the composition an amount of 2-substituted-3,3-diphenyl-2-propenoic acid derivative having the following general formula (I):

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is O, Y is O, and Z is a $C_{16}$ to $C_{50}$ straight or branched chain, substituted or unsubstituted, conjugated or non-conjugated hydrocarbon.

37. The method of claim 36, wherein the $R_{11}OH$ is selected from the group consisting of a substituted or unsubstituted siloxane and a substituted or unsubstituted organosiloxane.

38. The method of claim 36, wherein said 2-substituted-3,3-diphenyl-2-propenoic acid derivative of said general formula (I) is 2-cyano-3,3-diphenyl-2-propenoic acid with $C_{16}$ to $C_{50}$ straight or branched chain, substituted or unsubstituted, conjugated or non-conjugated hydrocarbon having esters.

39. The method of claim 38, wherein said 2-cyano-3,3-diphenyl-2-propenoic acid with $C_{16}$ to $C_{50}$ straight or branched chain, substituted or un-substituted, conjugated or non-conjugated hydrocarbon is $C_{20}$-$C_{40}$ cyano diphenyl propionate.

40. The method of claim 36, wherein the sunscreen active is selected from the group consisting of dibenzoylmethane, terephthalylidene dicamphor sunfonic acid, PABA, cinoxate, dioxybenzone, homosalate, menthylanthranilate, octocrylene, octyl methoxycinnamate, octyl salicylate, oxybenzone, padimate O, phenylbenzimidazole sulfonic acid, sulisobenzone, titanium dioxide, zinc oxide, trolamine salicylate, octyl triazone, DEA methoxycinnamate, drometrizole trisiloxane, oxybenzone, octyl methoxycinnamate, octyl salicylate, homomenthyl salicylate, octyl dimethyl PABA, TEA salicylate, 4-methyl benzilidene camphor, ethyl PABA, hydroxy methylphenyl benzotriazole, methylene bis-benzotriazoyltetramethylbutylphenol, zinc oxide, titanium oxide, bis-ethylhexyloxyphenol methoxyphenol triazine, and any derivatives thereof, and any combinations thereof.

41. The method of claim 40, wherein the sunscreen active is dibenzoylmethane or a derivative thereof.

42. A method of synergistically enhancing the UV absorbance of a topical sunscreen composition having a sunscreen active and a cosmetically acceptable vehicle, the method comprising introducing into the composition an amount of a compound having the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is selected from the group consisting of NH, NR, O and S, Y is selected from the group consisting of NH, NR, O and S, and Z is a $C_{16}$ to $C_{50}$ straight or branched chain, substituted or unsubstituted, conjugated or non-conjugated hydrocarbon.

43. A method of synergistically enhancing the UV absorbance of a topical sunscreen composition having a sunscreen active and a cosmetically acceptable vehicle, the method comprising introducing into the composition an amount of 2-substituted-3,3-diphenyl-2-propenoic acid derivative having the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is O, Y is O, and Z is a $C_{16}$ to $C_{50}$ straight or branched chain, substituted or unsubstituted, conjugated or non-conjugated hydrocarbon.

44. The method of claim 43, wherein the $R_{11}OH$ is selected from the group consisting of a substituted or unsubstituted siloxane and a substituted or unsubstituted organosiloxane.

45. The method of claim 43, wherein said 2-substituted-3,3-diphenyl-2-propenoic acid derivative of said general formula (I) is 2-cyano-3,3-diphenyl-2-propenoic acid with $C_{16}$ to $C_{50}$ straight or branched chain, substituted or unsubstituted, conjugated or non-conjugated hydrocarbon having esters.

46. The method of claim 45, wherein said 2-cyano-3,3-diphenyl-2-propenoic acid with $C_{16}$ to $C_{50}$ straight or branched chain, substituted or un-substituted, conjugated or non-conjugated hydrocarbon is $C_{20}$-$C_{40}$ cyano diphenyl propionate.

47. The method of claim 43, wherein the sunscreen active is selected from the group consisting of dibenzoylmethane, terephthalylidene dicamphor sunfonic acid, PABA, cinoxate, dioxybenzone, homosalate, menthylanthranilate, octocrylene, octyl methoxycinnamate, octyl salicylate, oxybenzone, padimate O, phenylbenzimidazole sulfonic acid, sulisobenzone, titanium dioxide, zinc oxide, trolamine salicylate, octyl triazone, DEA methoxycinnamate, drometrizole trisiloxane, oxybenzone, octyl methoxycinnamate, octyl salicylate, homomenthyl salicylate, octyl dimethyl PABA, TEA salicylate, 4-methyl benzilidene camphor, ethyl PABA, hydroxy methylphenyl benzotriazole, methylene bis-benzotriazoyltetramethylbutylphenol, zinc oxide, titanium dioxide, bis-ethylhexyloxyphenol methoxyphenol triazine, and any derivatives thereof, and any combinations thereof.

48. The method of claim 47, wherein the sunscreen active is dibenzoylmethane or a derivative thereof.

49. A method of enhancing the photostability of a sunscreen active in a topical sunscreen composition comprising introducing into the composition an amount of a compound having the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, $X_4$ is selected from the group consisting of NH, NR, O and S, Y is selected from the group consisting of NH, NR, O and S, and Z is a $C_{16}$ to $C_{50}$ straight or branched chain, substituted or unsubstituted, conjugated or non-conjugated hydrocarbon.

50. A method of enhancing the photostability of a sunscreen active in a topical sunscreen composition comprising introducing into the composition an amount of 2-substituted-3,3-diphenyl-2-propenoic acid derivative having the following general formula (I):

(I)

wherein each $X_1$, $X_2$ and $X_3$ are independently selected from the group consisting of cyclic and acyclic, saturated and unsaturated, substituted and unsubstituted, alkyls, aryls, amides, amines, hydroxyls, alkoxyls, halogens, hydrogens, carboxyls, nitriles, nitros, sulfonyls, anionic and cationic groups, x4 is O, Y is O, and Z is a $C_{16}$ to $C_{50}$ straight or branched chain, substituted or unsubstituted, conjugated or non-conjugated hydrocarbon.

51. The method of claim 50, wherein the $R_{11}OH$ is selected from the group consisting of a substituted or unsubstituted siloxane and a substituted or unsubstituted organosiloxane.

52. The method of claim 50, wherein said 2-substituted-3,3-diphenyl-2-propenoic acid derivative of said general formula (I) is 2-cyano-3,3-diphenyl-2-propenoic acid with $C_{16}$ to $C_{50}$ straight or branched chain, substituted or unsubstituted, conjugated or non-conjugated hydrocarbon having esters.

53. The method of claim 52, wherein said 2-cyano-3,3-diphenyl-2-propenoic acid with $C_{16}$ to $C_{50}$ straight or branched chain, substituted or un-substituted, conjugated or non-conjugated hydrocarbon is $C_{20}$-$C_{40}$ cyano diphenyl propionate.

54. The method of claim 50, wherein the sunscreen active is selected from the group consisting of dibenzoylmethane, terephthalylidene dicamphor sunfonic acid, PABA, cinoxate, dioxybenzone, homosalate, menthylanthranilate, octocrylene, octyl methoxycinnamate, octyl salicylate, oxybenzone, padimate O, phenylbenzimidazole sulfonic acid, sulisobenzone, titanium dioxide, zinc oxide, trolamine salicylate, octyl triazone, DEA methoxycinnamate, drometrizole trisiloxane, oxybenzone, octyl methoxycinnamate, octyl salicylate, homomenthyl salicylate, octyl dimethyl PABA, TEA salicylate, 4-methyl benzilidene camphor, ethyl PABA, hydroxy methylphenyl benzotriazole, methylene bis-benzotriazoyltetramethylbutylphenol, zinc oxide, titanium dioxide, bis-ethylhexyloxyphenol methoxyphenol triazine, and any derivatives thereof, and any combinations thereof.

55. The method of claim 54, wherein the sunscreen active is dibenzoylmethane or a derivative thereof.

56. A method of enhancing the substantivity, waterproofness, sweat resistance and rub off resistance in a topical sunscreen composition by applying to the skin of a user a composition of claim 1.

57. A method of enhancing the substantivity, waterproofness, sweat resistance and rub off resistance in a topical sunscreen composition by applying to the skin of a user a composition of claim 6.

* * * * *